(12) United States Patent
Wu et al.

(10) Patent No.: US 9,671,338 B1
(45) Date of Patent: Jun. 6, 2017

(54) WATER QUALITY SENSOR FOR HOUSEHOLD APPLIANCE

(71) Applicant: SOLTEAM OPTO, INC., Taoyuan (TW)

(72) Inventors: Shang-Jung Wu, Taoyuan (TW); Chun-Yen Wu, Taoyuan (TW); Chin-Feng Chen, Taoyuan (TW)

(73) Assignee: SOLTEAM OPTO, INC., Taoyuan (TW)

( * ) Notice: Subject to any disclaimer, the term of this patent is extended or adjusted under 35 U.S.C. 154(b) by 0 days.

(21) Appl. No.: 15/053,995

(22) Filed: Feb. 25, 2016

(51) Int. Cl.
*G01N 21/00* (2006.01)
*G01N 21/49* (2006.01)
*G01N 27/07* (2006.01)
*G01N 33/18* (2006.01)
*A47L 15/42* (2006.01)
*D06F 39/00* (2006.01)

(52) U.S. Cl.
CPC .......... *G01N 21/49* (2013.01); *A47L 15/4297* (2013.01); *D06F 39/004* (2013.01); *G01N 27/07* (2013.01); *G01N 33/18* (2013.01); *A47L 2401/10* (2013.01); *D06F 2202/02* (2013.01); *G01N 2201/126* (2013.01)

(58) Field of Classification Search
CPC ... H01J 37/32935; G01N 21/64; G01N 21/68; G01N 2015/1037; G01J 3/02
USPC .......................................................... 356/72
See application file for complete search history.

(56) References Cited

U.S. PATENT DOCUMENTS

| 5,974,213 | A | * | 10/1999 | Maruchi | G02B 6/0001 385/39 |
|---|---|---|---|---|---|
| 2005/0247992 | A1 | * | 11/2005 | Tsukamoto | H01L 27/14618 257/433 |
| 2007/0101772 | A1 | * | 5/2007 | Duncan | D06F 17/10 683/3 R |
| 2012/0308877 | A1 | * | 12/2012 | Hirai | H01M 2/024 429/184 |
| 2013/0016354 | A1 | * | 1/2013 | Wu | G01N 21/53 356/441 |
| 2013/0123139 | A1 | * | 5/2013 | Kim | B01L 3/5085 506/9 |
| 2013/0278921 | A1 | * | 10/2013 | Choi | G01N 21/85 356/51 |
| 2015/0084576 | A1 | * | 3/2015 | Magee | H02P 6/183 318/768 |

(Continued)

*Primary Examiner* — Tarifur Chowdhury
*Assistant Examiner* — Md M Rahman
(74) *Attorney, Agent, or Firm* — Haverstock & Owens LLP

(57) ABSTRACT

The present invention provides a water quality sensor for household appliance which is installed inside of a washing appliance, including a housing and a detecting module contained therein. The detecting module includes a light emitting element for emitting a detecting beam passing through the transparent panel, and a light receiving element for receiving a backscattered beam generated from the detecting beam and backscattered by the cleaning medium. The light emitting element and the light receiving element are positioned on a same plane of a circuit board parallel to the transparent panel, and the detecting beam emitted from the light emitting element is blocked by a sensor holder from being directly received by the light receiving element, such that the water quality sensor determines the water quality of the cleaning medium contained in the household appliance based on the backscattered beam.

15 Claims, 12 Drawing Sheets

(56) References Cited

U.S. PATENT DOCUMENTS

| | | | |
|---|---|---|---|
| 2015/0164301 A1* | 6/2015 | Bartloff | A47B 95/043 211/41.8 |
| 2015/0268742 A1* | 9/2015 | Park | G06F 3/03545 345/179 |
| 2016/0041038 A1* | 2/2016 | Geiger | G01J 5/046 250/338.1 |

* cited by examiner

WATER QUALITY SENSOR FOR HOUSEHOLD APPLIANCE

BACKGROUND OF THE INVENTION

Field of the Invention

The present invention relates to water quality sensors for household appliances. Particularly, the present invention relates to the water quality sensor utilizing backscattered light to determine the turbidity level of cleaning water in the household appliances to enhance the accuracy of turbidity detection, and also having a simple structure to reduce the fouling on the sensor.

Description of the Prior Art

With the development of technology, there are more and more household appliances for people to do housework in a time-saving fashion. Among these house appliances, washing appliances, such as the laundry machine and the dishwasher, are those utilizing liquid water containing detergent as the cleaning medium to clean articles, such that the efforts and time can be reduced compared to hand-washing.

Typically, washing appliances, e.g. the laundry machine and the dishwasher, are provided with the water quality sensor in the inner space for washing of the appliance, by which the turbidity or conductivity of the water can be determined. As disclosed in U.S. Pat. No. 5,596,408 and U.S. Pat. No. 6,771,373, a turbidity sensor has a housing having two finger protrusions which cleaning water is flowing in-between. The light emitting element and the light receiving element are face-to-face and separately positioned inside each finger protrusion of the housing. As the light emitting element generates a detecting beam passing through the transparent side of the housing, the particles in the water scatters away some portion of the detecting beam and allow the remaining portion to be transmitted through the water and be received by the light receiving element of the other side. So that by calculating the portion of detecting beam through the water and received by the light receiving element, the turbidity of the water can be determined. When the turbidity of water is detected at a predetermined level, the machine can be automatedly refilled with clean water to enhance the washing quality. However, turbidity detection becomes very inaccurate at low turbidity level. And, the fouling on the finger-type protrusion could also reduce the accuracy of detection and shorten the life-time of the sensor.

Also, a water quality sensor can further comprise a conductivity sensor. The conductivity sensor has two electrodes, which are controlled by a built-in microcontroller unit (MCU) of the washing appliance, to discharge in the cleaning medium. Generally, the velocity of electrons moving in water would be substantially constant, and may vary if there are ions (e.g. ions generated by the detergent dissolved in water) existing in the liquid water. In such case, an analog signal such as a voltage signal or a current signal would be obtained from the two electrodes by the MCU, and would be transmitted to an analog-to-digital converter (ADC). The analog signal would be converted by the ADC to a digital signal, such as a value of conductivity or a pH value. Compared to the constant conductivity or pH value of water in a general situation, the MCU could determine if there is any foreign ion existing in the liquid water based on the digital signal, so as to further determine if the washing needs to continue.

Nevertheless, with the increasing functionality of various washing appliances, it requires more and more sensors, such as a temperature sensor besides the turbidity sensor and the conductivity sensor mentioned above, to be configured and function within the washing appliance, and thereby the computing burden of the built-in MCU of the appliance would be significantly increased. In order to determine if one specific function of the washing appliance is to operate, the built-in MCU has to provide the control signals to the respective sensors, receive the analog signals returned from the respective sensors, transmit the respective analog signals to the ADC to convert these signals to a respective digital signal, and determine the functions of the washing appliance to be operate based on these digital signals. Such increased computing burden causes the possibility of error or abnormality for the built-in MCU.

The error or abnormality caused by the heavy computing burden of the built-in MCU may result in a malfunction thereof, and thereby the water quality sensor may keep discharging in the cleaning medium inside the washing appliance. In such case, the user will possibly get an electric shock from the washing appliance or the cleaning medium while touching the same.

A need thus exists for improved water quality sensors for improving the accuracy of detection, and for avoiding the error and abnormality of the built-in MCU of the household appliance that is caused by the increased computing burden of the MCU.

SUMMARY OF THE INVENTION

In view of the aforesaid drawbacks of the prior art, an improved water quality sensor for the household appliance is provided. The water quality sensor of the present invention is capable of improving the accuracy of turbidity detection by detecting the light backscattered by the particles in the cleaning medium, and having a simple structure to reduce the fouling effect to increase the lift-time of the sensor. The water quality sensor of the present invention is also capable of reducing the computing burden of the built-in microcontroller unit (MCU) of the household appliance by the configuration of microcontroller and analog-to-digital converter (ADC) on the circuit board of detecting module thereof.

According to one aspect of the present invention, the water quality sensor for a household appliance includes a housing forming an inner space and having at least one transparent panel in contacting to a cleaning medium of the household appliance, a circuit board having a microcontroller configured thereon, the circuit board being positioned within the inner space and housed by the housing, a light emitting element configured on the circuit board for emitting a detecting beam passing through the transparent panel, a light receiving element configured on the circuit board for receiving a backscattered beam generated from the detecting beam and backscattered by the cleaning medium, and a sensor holder attached to the circuit board and receiving the light emitting element and the light receiving element therein. The light emitting element and the light receiving element configured on the circuit board are positioned on a same plane, and the detecting beam emitted from the light emitting element is blocked by the sensor holder from being directly received by the light receiving element. In such manner, the water quality sensor determines the water quality of the cleaning medium contained in the household appliance based on the backscattered beam.

Preferably, the water quality sensor further includes an electrical sensor for determining a conductivity of the cleaning medium. Preferably, the electrical sensor includes at least one electrode to discharge in the cleaning medium.

Preferably, the transparent panel is formed with a window portion, and wherein the at least one electrode is extended through the window portion and electrically contacted with the cleaning medium. Alternatively, the transparent panel may be formed with at least one concave portion and a corresponding through-hole, and wherein the at least one electrode is contained within the at least one concave portion and extended through the through-hole.

Preferably, the water quality sensor further includes an analog-to-digital converter to convert an analog signal transmitted from the electrical sensor to a digital signal. The analog-to-digital converter is separated from the microcontroller and electrically connected thereto. Alternatively, the analog-to-digital converter may be built in the microcontroller.

Preferably, the circuit board is positioned on a plane parallel to the transparent panel, such that the detecting beam is permitted to pass along a path perpendicular to a flow direction of the cleaning medium.

Preferably, the sensor holder has a plurality of non-transparent walls surrounding the light emitting element, and an opening formed on a top thereof, and the detecting beam emitted by the light emitting element housed by the sensor holder is permitted to only pass the opening. Preferably, the top of the sensor holder is apart from the transparent panel by less than 5 mm.

Preferably, each of the non-transparent walls has a thickness ranged from 1 mm to 5 mm, and a height ranged from 2 mm to 10 mm.

Preferably, the distance between the light emitting element and the light receiving element, in particular, between the center of the light emitting element and the center of the light receiving element, is ranged from 3 mm to 10 mm.

Preferably, the housing includes a base and a cover attached thereto, and the transparent panel is configured on the base at a side opposite to the cover.

Preferably, the water quality is a turbidity level of the cleaning medium.

Preferably, the household appliance is a dishwasher or a laundry machine.

According to the invention, the water quality sensor includes an optical sensor which utilizes the backscattered light generated from a detecting beam emitting from the light emitting element and backscattered by the cleaning medium to determine the turbidity level of the cleaning medium in the household appliances, thereby enhancing the accuracy of turbidity detection. The water quality sensor according to the present invention is capable of reducing the fouling on the sensor with a simple structure, such that the life-time of the sensor is improved.

According to the present invention, the water quality sensor includes an electrical sensor in addition to the optical sensor. The optical sensor, which is constructed by the light emitting element and the light receiving element, and the electrical sensor may function to obtain a digital signal and a measurable analog signal from the cleaning medium, respectively. The analog signal obtained by the electrical sensor is transmitted to the ADC to be converted to an additional digital signal representing such as a conductivity of the cleaning medium. The converted digital signal is returned, along with the sensing digital vale obtained by the optical sensor, to the built-in MCU of the household appliance for the built-in MCU to determine if the washing process of the appliance shall continue. In such manner, the digital-converting of various analog signals and the data-computing by the built-in MCU could be eliminated to reduce the burden, such that the computing error or abnormality of the built-in MCU could be avoided.

Further, according to the present invention, the water quality sensor is provided with a detecting module constructed by the circuit board, the optical sensor configured on the circuit board, and the electrical sensor configured on the circuit board. The detecting module of the present invention further includes the microcontroller and the ADC which are configured on the circuit board of the detecting module. During the operation, the microcontroller of the detecting module is actuated and controlled by the built-in MCU of the household appliance to initiate the discharging of the two electrodes of the electrical sensor in the cleaning medium contained in the inner space for washing of the appliance, and to terminate the discharging of the two electrodes when a measurable analog signal is generated and detected. In such manner, the charges could be prevented from being accumulated inside the inner spacing for washing, so as to protect the user from getting an electric shock from the washing appliance or the cleaning medium while touching the same.

The foregoing aspects and other aspects of the present invention will be fully described with exemplary embodiments below by reference to the appended drawings.

DETAILED DESCRIPTION OF THE EMBODIMENTS

The present invention will be fully described by way of preferred embodiments and appended drawings to facilitate the understanding of the technical features, contents and advantages of the present invention and the effect to be achieved by the present invention. It will be understood that the appended drawings are merely schematic representations and may not be illustrated according to actual scale and precise arrangement of the implemented invention. Therefore, the scope of protection of the present invention shall not be construed based on the scale and arrangement illustrated on the appended drawings and limited thereto.

Figure 1:
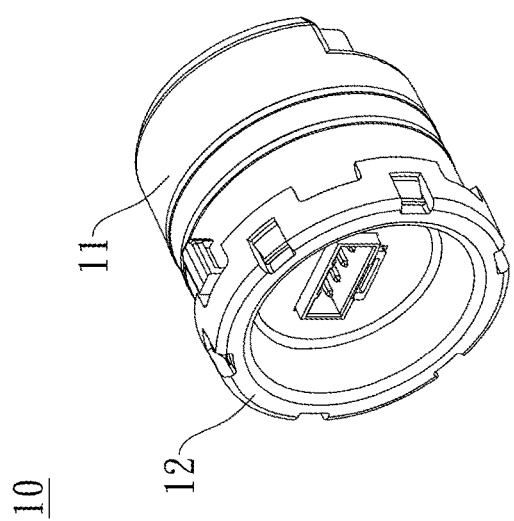
FIG. 1 is an assembled view showing the water quality sensor in accordance with a first embodiment of the present invention.
Figure 2:
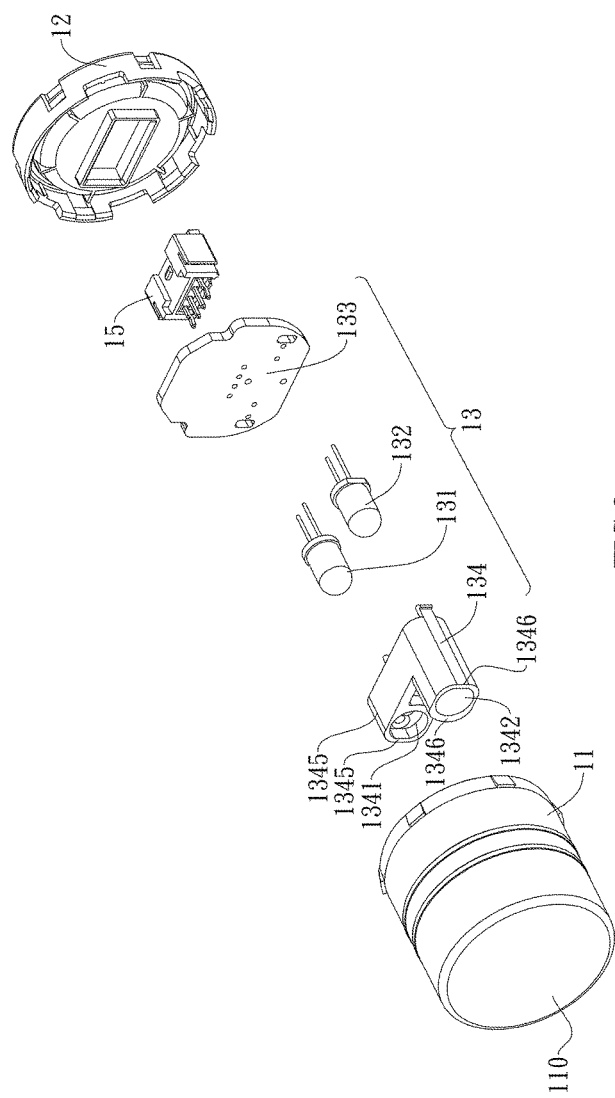
FIG. 2 is an exploded view of the water quality sensor of the first embodiment of the present invention.
Figure 3:
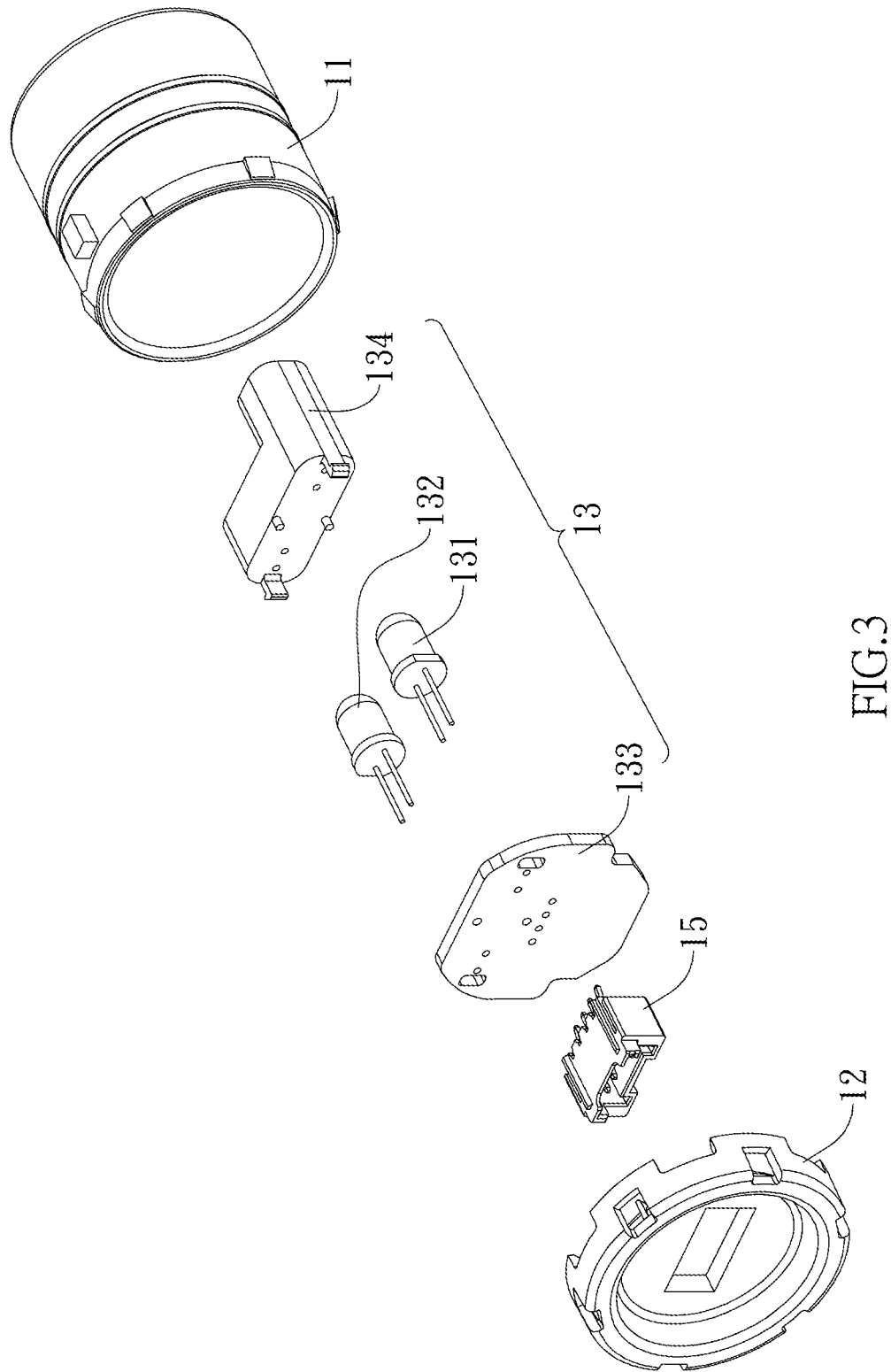
FIG. 3 is an exploded view of the water quality sensor of the first embodiment of the present invention obtained from a direction opposite to that as shown in FIG. 2.

FIGS. 1 and 2 are the perspective view and the exploded view showing the water quality sensor according to the first embodiment of the present invention, respectively. FIG. 3 is an exploded view of the water quality sensor of the first embodiment of the present invention that is viewed from a direction opposite to that as shown in FIG. 2. The water quality sensor of the present invention may be installed in the inner space of a household appliance for determining the water quality of a cleaning medium contained in the inner space for washing. As an illustrative example, the household appliance may be a laundry machine or a dishwasher, and the cleaning medium may be liquid water with a detergent contained therein. The water quality of the cleaning medium to be determined includes, but not limited to, the turbidity level or the luminosity of the cleaning medium. Based on the water quality determined by the sensor, the built-in microcontroller unit (MCU) of the household appliance may determine if the washing process is to continue.

Referring to FIGS. 1 to 3, the water quality sensor of the present invention includes the housing 10 and the detecting module 13 contained therein. The housing 10 is formed of a base 11 and a cover 12 attached to the base 11, and thereby an inner space 14 (as shown in FIG. 3) is formed for containing the detecting module 13. The base 11, which is hollow and is substantially cylinder-shaped, provides a substantial portion of the inner space 14 of the housing 10. The front face of the base 11, i.e. the face towards the inner space of the appliance, is transparent, and thus provides the housing 10 with a transparent panel 110. The transparent panel 110 is in contacting to the cleaning medium during the washing process of the appliance. The cover 12 is engaged with the base 11 at the side opposite to the transparent panel 110.

In this embodiment, the detecting module is an optical sensor 13 for detecting a digital signal, such as the turbidity level or the luminosity, of the cleaning medium. The digital signal is to be transmitted to the built-in MCU of a household appliance. Based on the digital signal from the detecting module (i.e. the optical sensor 13 in this embodiment), the built-in MCU of the household appliance may determine if there are too many suspended particles existing in the cleaning medium, and thereby determine if the washing process is to continue.

The detecting module includes a light emitting element 131 and a light receiving element 132, a circuit board, such as a printed circuit board (PCB) 133, and a sensor holder 134. The light emitting element 131 for emitting a detecting beam and the light receiving element 132 for receiving a backscattered beam generated from the detecting beam and backscattered by the cleaning medium of the household appliance are arranged on the PCB 133 at the same plane and are housed by the sensor holder 134. The sensor holder 134 is attached to the PCB 133, and receives the light emitting element 131 and the light receiving element 134 therein. The sensor holder 134 may be formed by a plurality of walls 1345 that are non-transparent or opaque. The plurality of walls surround the light emitting element 131, and thus an opening 1341 is formed on the top of the sensor holder 134 for the detecting beam to pass. Similarly, the light receiving element is also surrounded by a plurality of walls 1346, and an opening 1342 is formed on the sensor holder 134 for the light receiving element 132 to receive the light in a specific direction, i.e. in a straight ahead direction. In other words, through the openings 1341 and 1342 formed on the sensor holder 134, the light emitting element 131 and the light receiving element 132 are merely exposed at the top of the sensor holder 134, such that the detecting beam emitted by the light emitting element 131 can only pass through the top of the sensor holder 134, and is blocked by the sensor holder 134 in a lateral direction. That is, through the design of sensor holder 134, the detecting beam emitted by the light emitting element 131 is not allowed to be directly received by the light receiving element 132.

According to the present invention, the PCB 133 is positioned on a plane parallel to the transparent panel 110, such that the detecting beam would pass along a path perpendicular to a flow direction of the cleaning medium inside the household appliance.

The water quality sensor of the present invention further includes a connector 15 mounted at one end thereof to the PCB 133. The other end of the connector 15 may be exposed through the cover 12 of the water quality sensor, so as to electrically connect the water quality sensor to a power source for operation, and to communicate with the built-in MCU of the household appliance.

Figure 4:
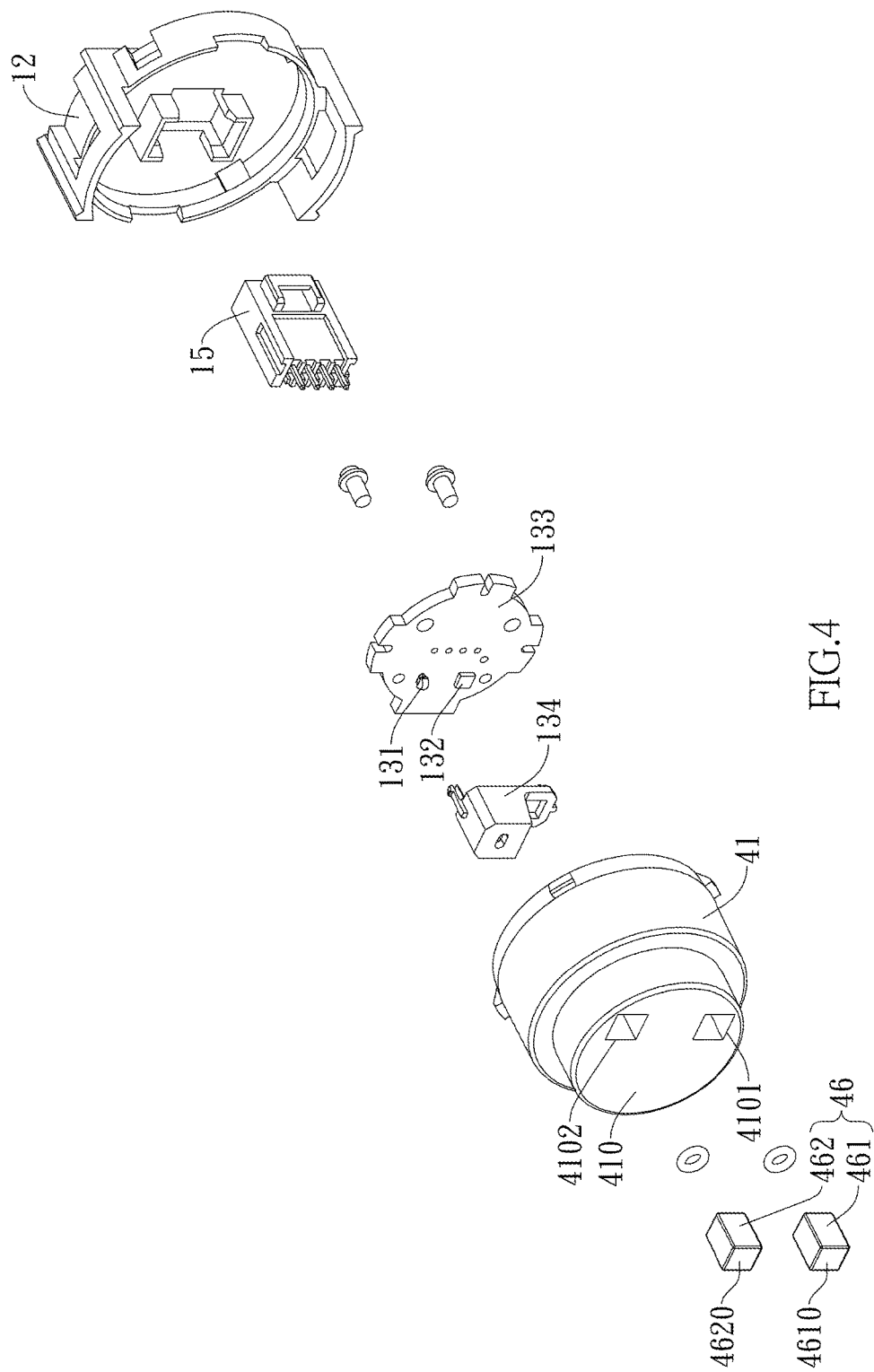
FIG. 4 is an exploded view showing the water quality sensor in accordance with a second embodiment of the present invention.
Figure 5:
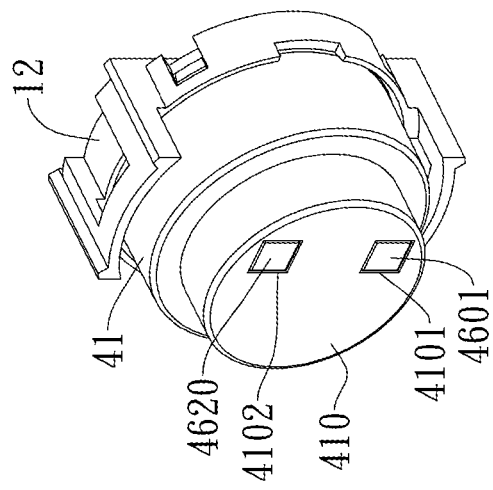
FIG. 5 is an assembled view showing the water quality sensor of the second embodiment.

FIG. 4 is an exploded view showing the water quality sensor in accordance with a second embodiment of the present invention, and FIG. 5 is an assembled view of the water quality sensor of the second embodiment. In this embodiment, the components of the water quality sensor are similar to those as of the first embodiment except for the design of base 41 and the configuration of electrical sensor 46. In this embodiment, the detecting module 13 includes not only the optical sensor of light emitting element 131 and light receiving element 132, but also an electrical sensor 46 having two electrodes 461 and 462 as shown in FIG. 4. The two electrodes 461 and 462 of the electrical sensor 46 function to discharge in the cleaning medium upon the control of built-in MCU of the household appliance, and to determine a conductivity of the cleaning medium. The base 41 of the housing of the water quality sensor is different from the base 11 as shown in FIG. 2 by the window portions 4101 and 4102 formed on the transparent panel 410. As shown in FIGS. 4 and 5, the two electrodes 461 and 462 are housed by the base 41, except for their top faces 4610 and 4620. The two electrodes 461 and 462 are arranged as being extended through the respective window portions 4101 and 4102, with their respective top faces 4610 and 4620 being flushed with the transparent panel 410, and are exposed to and electrically contacted the cleaning medium the cleaning medium at their respective top faces 4610 and 4620, so as to determine the conductivity of the cleaning medium for the built-in MCU to determine if the washing process is to continue.

The operation and the components of the water quality sensor of the present invention are further described with reference to FIGS. 6 to 8.

Figure 6:
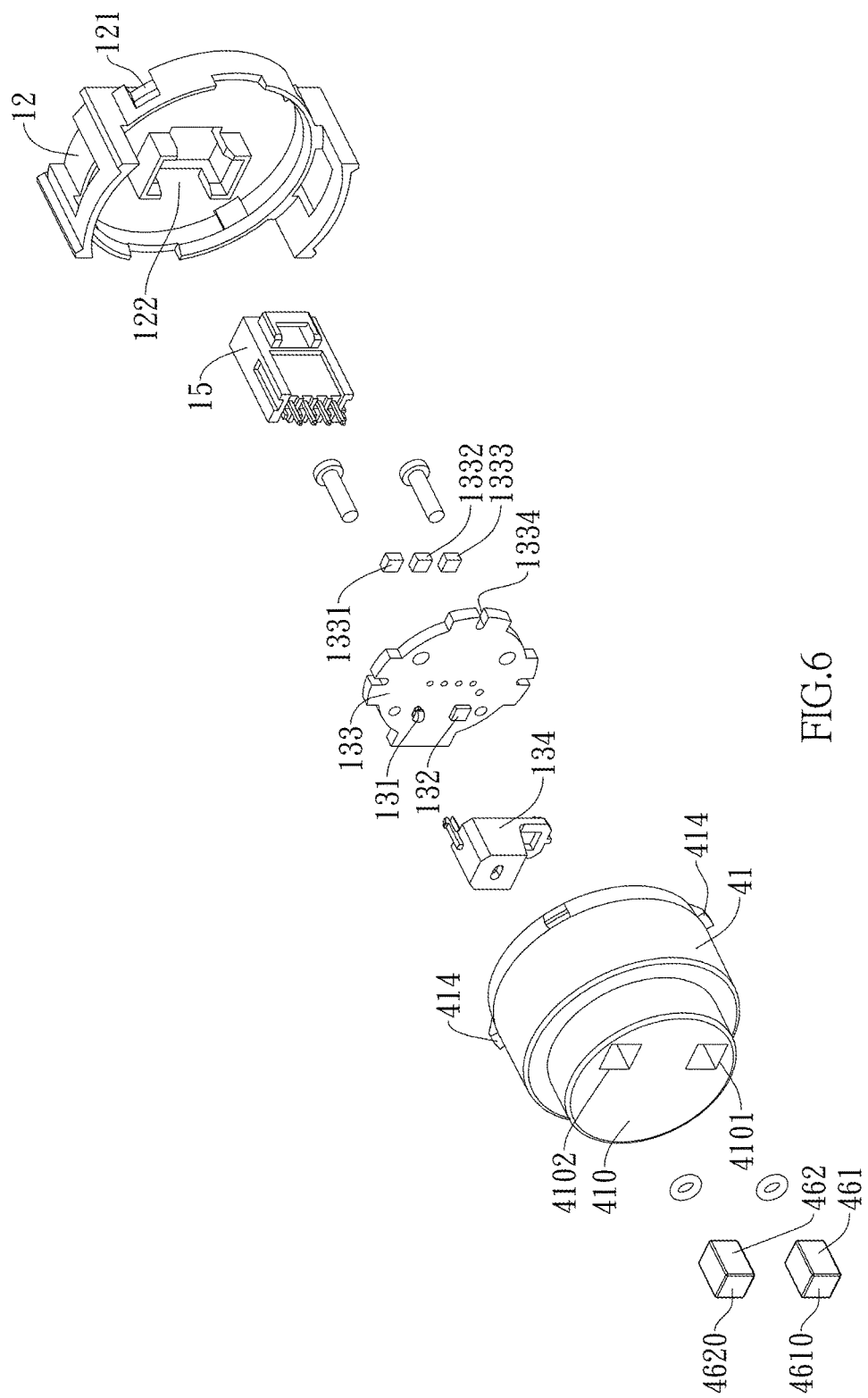
FIG. 6 is an exploded view showing the water quality sensor of the second embodiment of the present invention in greater detail.
Figure 7:
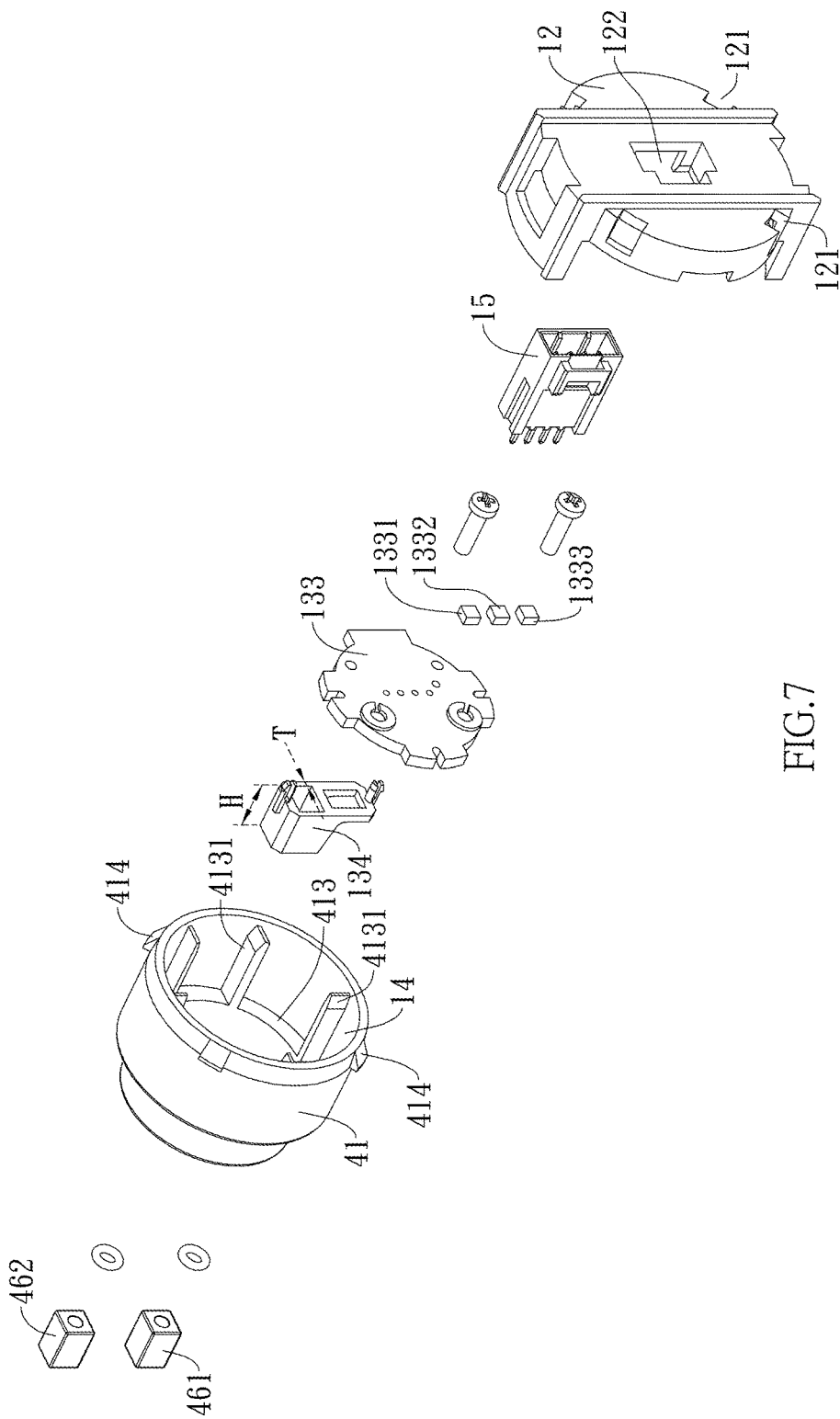
FIG. 7 is an exploded view of the water quality sensor of the second embodiment of the present invention obtained from a direction opposite to that as shown in FIG. 6.
Figure 8:
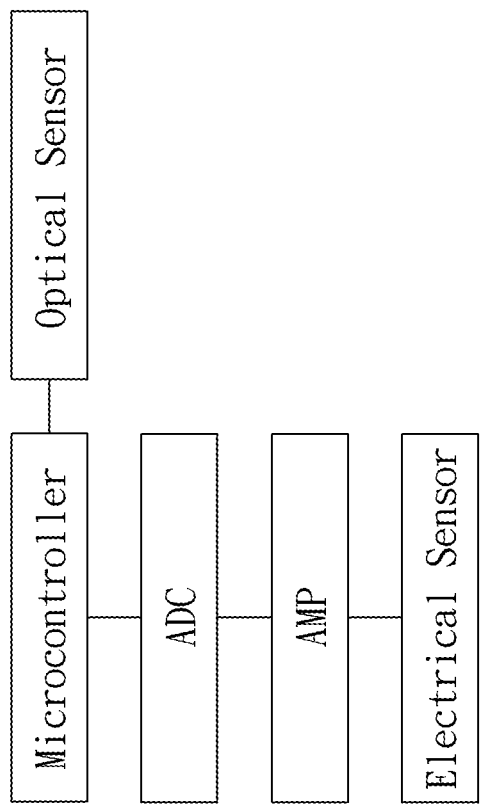
FIG. 8 schematically shows the circuitry of the water quality sensor of the second embodiment of the present invention.

FIGS. 6-7 are exploded views showing the components of the water quality sensor according to the second embodiment of the present invention in greater detail, wherein FIG. 7 is viewed from a direction opposite to that as shown in FIG. 6, and FIG. 8 schematically shows the circuitry of the water quality sensor of the second embodiment of the present invention.

Referring to FIGS. 6-7, in addition to the components and structure as shown in FIGS. 4-5, a detailed design of the water quality sensor of the invention is illustrated.

The water quality sensor of the present invention includes the housing 10 and the detecting module contained therein. The housing 10 is formed of a base 41 and a cover 12 attached to the base 41, and thereby an inner space 14 (as shown in FIG. 7) is formed for containing the detecting module 13. The inner space 14 is open at one side thereof. The front face of the base 41 is transparent, and thus provides the housing 10 with a transparent panel 410. The cover 12 is engaged with the base 41 at the side opposite to the transparent panel 410, i.e. at the side at which the inner space 14 is open. As illustrated above, the transparent panel 410 is formed with the window portions 4101 and 4102 thereon for allowing the respective two electrodes 461 and 462 to extend therethrough. The top faces 4610 and 4620 of the two electrodes 461 and 462 are flushed with the transparent panel 410, so that the two electrodes 461 and 462 are exposed to and electrically contacted the cleaning medium merely at the respective top faces 4610 and 4620 thereof to determine the conductivity of the cleaning medium for the built-in MCU to determine if the washing process is to continue.

The interior of the base 41 is formed with a stopping face 413 and a plurality of posts 4131. The posts 4131 are formed as extending from the stopping face 413 toward the open side of the base 41. On the side of the base 41 that is opposite to the transparent panel 410, the outer periphery of the base 41 is formed with a plurality of engaging structures 414. These engaging structures 414 are formed as being corresponding to the plurality of engaging portions 121 of the cover 12, so as to provide a rigid combination of the base 41 and the cover 12.

The engaging portions 121 are formed on the cover 12 for receiving the plurality of engaging structures 414 of the base 41, thereby the base 41 and the cover 14 are engaged with each other. Further, on the inner face of the cover 12, i.e. the face towards the inner space 14, a receiving portion 122 is formed to receiving the connector 15, such that the connector 15 mounted at one end thereof to the PCB 133 may be exposed through the cover 12 to electrically connect the water quality sensor to a power source for operation, and to communicate with the built-in MCU of the household appliance.

In this preferred embodiment, the detecting module of the water quality sensor includes the optical sensor 13 and the electrical sensor 46. On the PCB 133, a microcontroller 1331, an analog-to-digital converter (ADC) 1332 and an amplifier 1333 are configured and electrically connected thereto. Furthermore, the profile of PCB 133 may be designed and shaped for corresponding to the interior of the base 41 and the interior of the cover 12, so as to be rigidly positioned in the inner space 14 formed by base 41 and the cover 12. For example, the periphery of the PCB 133 may be provided with plural notches 1334 to engage with the corresponding posts 4131 of the base 41.

As for the optical sensor 13 including the light emitting element 131 and the light receiving element 132, the light emitting element 131 and the light receiving element 132 are arranged on the PCB 133 at the same plane, and are housed by the sensor holder 134. In more specific, the sensor holder 134 is formed of a plurality walls (e.g. the walls 1345 and 1346 as shown in FIG. 2) surrounding the light emitting element 131 and the light receiving element 132. The height of the walls surrounding the light emitting element 134, as indicated by "H" in FIG. 7, is ranged from 2 mm to 10 mm, and the thickness thereof, as indicated by "T" in FIG. 7, is ranged from 1 to 5 mm. The light emitting element 131 and the light receiving element 132 are electrically connect to the PCB 133 and thus to the microcontroller 1331, and the distance between the centers of the respective light emitting element 131 and the light receiving element 132 is ranged from 3 mm to 10 mm.

The profile of the sensor holder 134 may be designed for rigidly mounting to the PCB 133. For example, the sensor holder 134 may be formed with a protruding portion 1341, which extends through the mounting hole 1335 of the PCB and provides a rigid engagement thereby when the water quality sensor is assembled.

In this preferred embodiment, the sensor holder 134 is formed by plural walls made of an opaque material, and has openings 1341 and 1342 formed on the top thereof, so as to make the light emitting element 131 and the light receiving element 132 exposed at the top of the sensor holder 134. In such manner, the detecting beam emitted by the light emitting element 131 can only pass through the top of the sensor holder 134, and is blocked by the sensor holder 134 in a lateral direction. That is, through the design of sensor holder 134, the detecting beam emitted by the light emitting element 131 is not allowed to be directly received by the light receiving element 132.

In this preferred embodiment, the two electrodes 461 and 462 of the electrical sensor 46 are housed by the base 41, and are expose to and electrically contacted the cleaning medium at the respective top faces 4610 and 4620 thereof through the window portions 4101 and 4102 on the transparent panel 410. The two electrodes 461 and 462 are positioned in such a way that the top faces 4610 and 4620 thereof are flushed with the transparent panel 410.

The electrical sensor 46 is electrically connected to the PCB 133 and thus to the ADC 1332. The amplifier 1333 is electrically connected between the two electrodes 461 and 462 and the ADC 1332. The connector 15, as illustrated, is mounted at one end thereof to the PCB 133, and thus electrically connected to the PCB 133 and the microcontroller 1331. The connector 15 may be exposed through the cover 12 to electrically connect the water quality sensor to a power source for operation, and to communicate with the built-in MCU of the household appliance.

Typical water-repellent elements, such as the washers and O-rings, may be used in the present invention to prevent the interior components of the water quality sensor from being exposed to the cleaning medium. Preferably, when assembling the water quality sensor of the present invention, it is able to fill the interior of the base 41 with silicon resin prior to attaching the cover 12 to the base 41, to avoid the detecting module of the water quality sensor from contacting the liquid water or the cleaning medium.

In this preferred embodiment, the ADC 1332 is a single device that is separated from the microcontroller 1331 but is electrically connected thereto through the connection to the PCB 133. Referring to FIG. 8 as well, the optical sensor 13, including the light emitting element 131 and the light receiving element 132 mounted on the PCB 133, is electrically connected to the microcontroller 1331, and also, the electrical sensor 46 is electrically connected to the microcontroller 1331. The ADC 1332 is individual and separated from the microcontroller 1331, such that an electrical connection between the microcontroller 1331 and the ADC 1332 is required. Furthermore, the amplifier 1333 is also a single device mounted on the PCB 133, and is electrically connected between the ADC 1332 and the electrical sensor 46. Such configuration is merely one illustrative example for the circuitry of the water quality sensor of the present invention.

Figure 9:
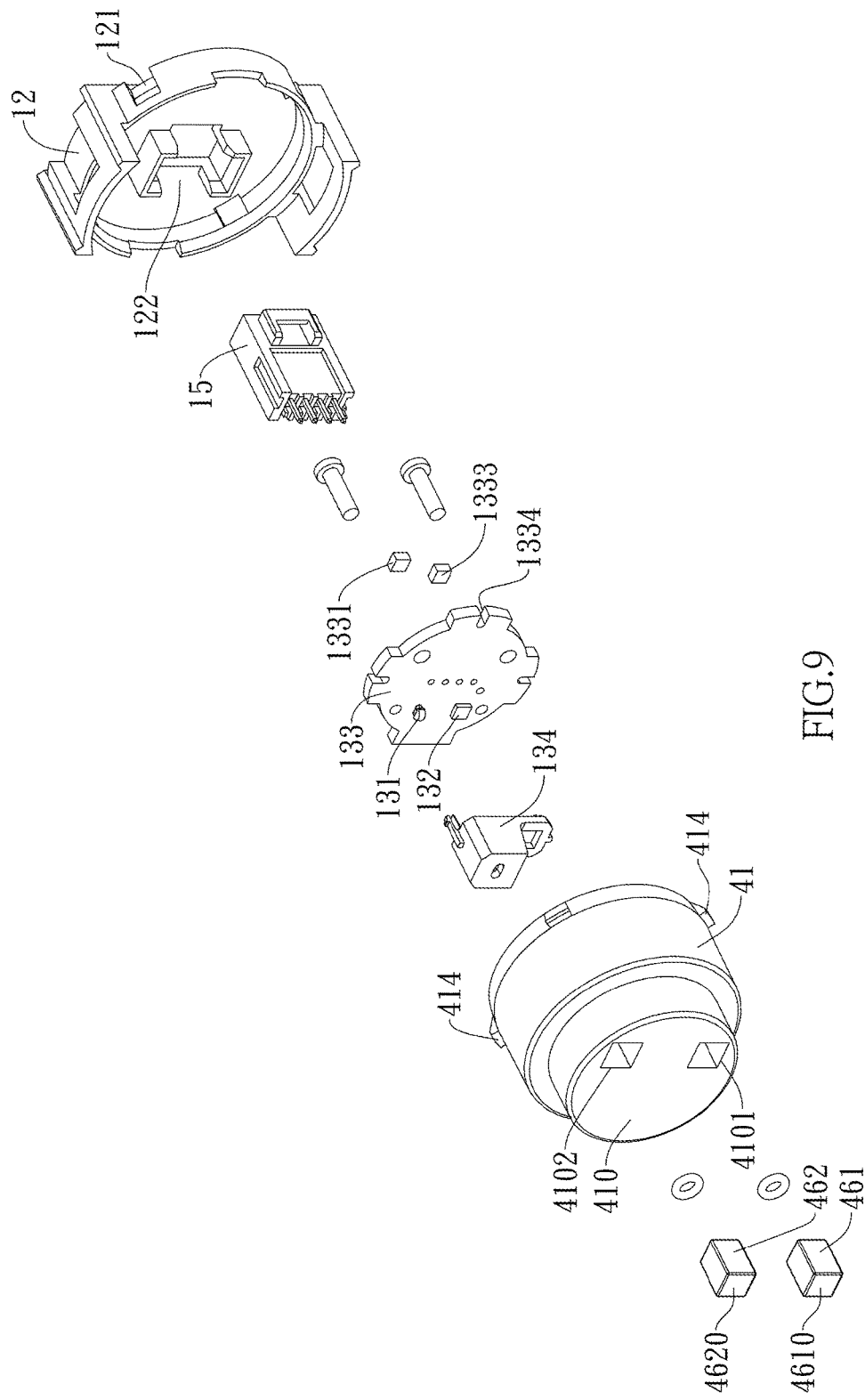
FIG. 9 is an exploded view of the water quality sensor of a third embodiment of the present invention.
Figure 10:
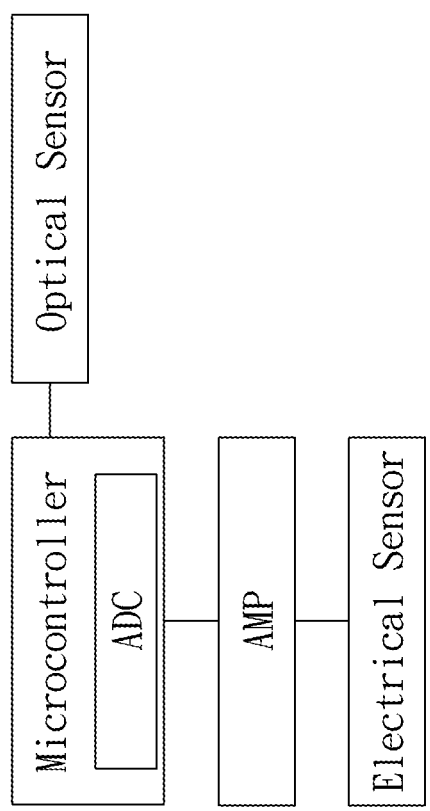
FIG. 10 schematically shows the circuitry of the water quality sensor of the third embodiment of the present invention.

As an alternative, FIGS. 9 and 10 show the water quality sensor according to a third embodiment of the present invention. The components of the water quality sensor as shown in FIG. 9 are similar to those as shown in FIG. 6 except for lacking a single ADC. In this embodiment, the ADC 1332 is integrated to the microcontroller 1331, which is electrically connected to the optical sensor 13. Also, the amplifier 1333 is electrically connected between the microcontroller 1331 and the electrical sensor 46.

According to the present invention, the optical sensor 13 is used for determine the water quality such as the turbidity of a cleaning medium in the household appliance, such as the laundry machine or the dishwasher. The water quality sensor of the present invention is installed in the inner space for washing of the appliance, in such a way that the transparent panel 110 (or 410) is arranged to face toward the inner space for washing of the appliance. The power to the water quality sensor is provided from the appliance, through the connection of connector 15, to power on the detecting module of the water quality sensor. The connector 15 is also electrically connected to the built-in MCU of the appliance. When the washing process is initiated, the built-in MCU will control the microcontroller 1331 to control the operation of the light emitting element 131. The light emitting element 131 operates to emit a detecting beam, passing through the through-hole 1341 of the sensor holder 134 to the liquid water or the cleaning medium contained in the inner space for washing of the laundry machine or dishwasher.

Under a normal situation, the reflection of the detecting beam in the liquid water is relatively weak. On the contrary, when there are particles existing in the liquid water, such as dirt, sands or undissolved soap powders, a multi-reflection effect, of the detecting beam will occur, and a backscattered beam will be generated thereby. In this way, the microcontroller 1331 detects the light beam in water through the light receiving element 132 to determine a digital signal, such as the turbidity or the luminosity, of the liquid water. The digital signal is transmitted to the built-in MCU of the household appliance for the built-in MCU to determine if there are too many suspended particles existing in the cleaning medium, and thereby determine if the washing is to continue.

Particularly, according to the present invention, the light emitting element 131 and the light receiving element 132 are exposed at the top of the sensor holder 134, and are arranged on the printed circuit board 133 at the same plane and housed by the sensor holder 134. Therefore, the detecting beam emitted by the light emitting element 131 can only pass through the top of the sensor holder 134, and will be blocked by the sensor holder 134 in a lateral direction. That is, by means of the present invention, the detecting beam emitted by the light emitting element 131 is not allowed to be directly received by the light receiving element 132. The light receiving element 132 of the sensor module 13 merely receives the backscattered beam that is generated from the detecting beam due to the multi-reflection effect.

In addition to the optical sensor 13, the built-in MCU of the household appliance may control the microcontroller 1331 to control the operation of the electrical sensor 46. The two electrodes 461 and 462 of the electrical sensor 46 are controlled by the microcontroller 1331 to discharge. Under a normal situation, the velocity of electrons moving in water would be substantially constant, and may vary if there are ions (e.g. ions generated by the detergent or soap powders dissolved in water) existing in the liquid water (or the cleaning medium). In this way, the microcontroller 1331 may detect the electrons in the liquid water through the two electrodes 461 and 462 to obtain a measurable analog signal, e.g. a voltage signal or a current signal. The analog signal would be amplified by the amplifier 1333, and converted by the ADC 1332 to a digital signal, such as a value of conductivity or a pH value. The digital signal converted from the analog signal will be transmitted by the microcontroller 1331 to the built-in MCU of the household appliance, for the built-in MCU to determine if there are foreign ions existing in the cleaning medium, and thereby determine if the washing is to continue.

Figure 11:
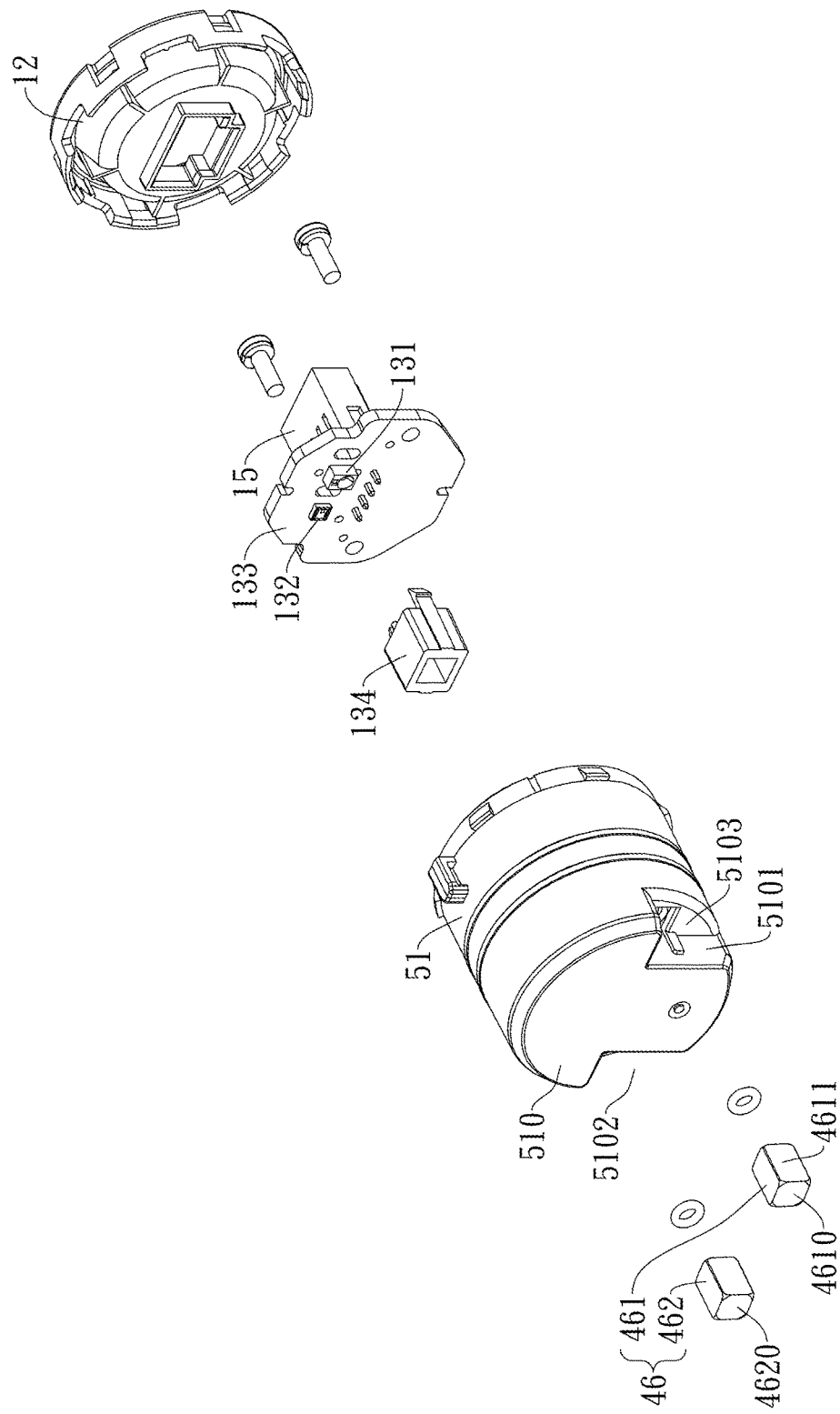
FIG. 11 is an exploded view of the water quality sensor of a fourth embodiment of the present invention.

According to the present invention, the accuracy of detection by the electrodes may be enhanced by increasing the area of the electrode that is exposed to the liquid water. Referring to FIG. 11, an exploded view of the water quality sensor according to a fourth embodiment of the present invention is shown, wherein the components of this embodiment are similar to those as shown in FIG. 4 except for the design of transparent panel 510 of the base 51. In this embodiment, the transparent panel 510 of the water quality sensor is provided with the concave portions 5101 and 5102 formed thereon. Corresponding to the two concave portions 5101 and 5102, there are two through-holes (one of which is indicated by 5103, and the other is not shown in FIG. 12) formed on the transparent panel 510 for containing the electrodes 461 and 462 therein. The electrodes 461 and 462 are extended through the respective through-holes 5103, and are thus exposed to and electrically contacted the cleaning medium, so as to determine the conductivity of the cleaning medium for the built-in MCU to determine if the washing is to continue.

Figure 12:
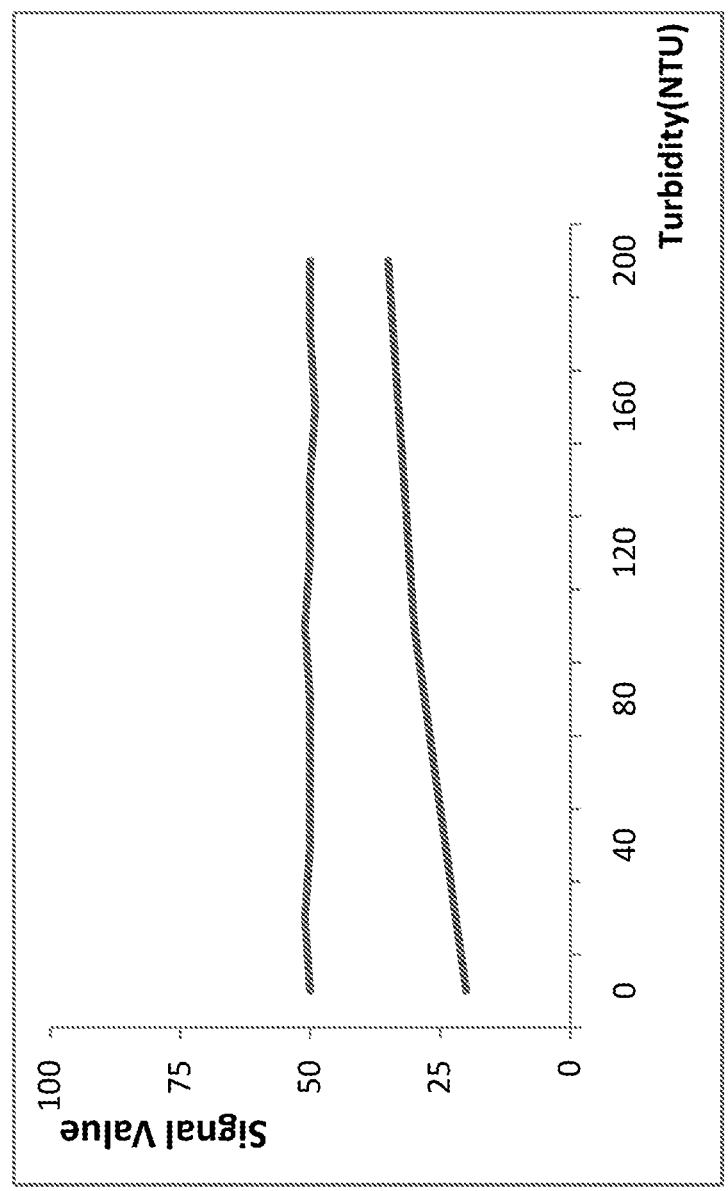
FIG. 12 depicts the comparison of the water quality sensor according to the present invention to the conventional water quality sensor, wherein Curve A shows a plot of the readings taken from the conventional water quality sensor, and Curve B shows a plot of the readings taken from the water quality sensor of the present invention.

In this embodiment, not only the top faces 4610 and 4620, but also the side faces (one of which is indicated by 4611, and the other is not shown in FIG. 12) of the electrodes 461 and 462, are exposed to cleaning medium due to the design of concave portions 5101 and 5102 of the transparent panel 510. Compared to the embodiment as shown in FIG. 4, the two electrodes 461 and 462 extending through the through-holes 5103 at the concave portions 5101 and 5102 are exposed to and electrically contacted the cleaning medium with a greater area, thereby increasing the intensity of measurable analog signals obtained by the electrodes. Therefore, the accuracy of detection of the electrical sensor is improved.

According to the present invention, the inner space formed by the base of the housing is provided for accommodating the PCB of the detecting module of the water quality sensor on which the microcontroller, the ADC, the optical sensor, and the electrical sensor are mounted. The optical sensor and the electrical sensor are positioned and arranged on one side of the PCB that is facing toward the transparent panel. On the other side of the PCB, the connector is mounted thereto, and is exposed through the receiving portion of the cover for electrical connection and communication. The analog signals obtained by the electrical sensor are transmitted to the ADC for being converted to digital signals. Such digital signals, e.g. the conductivity of cleaning medium, and the digital signal obtained by the sensor module, e.g. the turbidity or luminosity of cleaning medium, are transmitted by the microcontroller to the built-in MCU of the household appliance for the built-in MCU to determine if the washing is to continue. In such manner, the built-in MCU has no need to carry out the analog-to-digital conversion and the computation. Therefore, the computing burden of the built-in MCU is reduced, and the error or abnormality thereof may be mitigated.

According to the present invention, when a measurable analog signal is obtained from the electrical sensor, the microcontroller of the detecting module would control the two electrodes of the electrical sensor to stop discharging in the liquid water. In this manner, the accumulation of charges inside the inner space for washing of the appliance is avoided, so that the user will not get an electric shock from the washing appliance or the liquid water while touching the same.

One further advantage of the present invention is that, the light emitting element and the light receiving element of the optical sensor are housed by the sensor holder that is not transparent, and are merely exposed at the tops through the through-holes formed on the sensor holder. In this way, the detecting angle of the optical sensor can be well controlled, such that the accuracy of detection thereof can be improved.

Besides, the detecting beam emitted from the light emitting element is blocked by the sensor holder in a lateral direction, such that the detecting beam is not allowed to be directly received by the light receiving element. Therefore, the saturation of light receiving element caused by the cross-talk between the light emitting element and the light receiving element is avoided, and the accuracy of detection of the optical sensor can be improved.

FIG. 12 depicts the comparison of the water quality sensor according to the present invention to the conventional water quality sensor (as indicated by U.S. Pat. No. 5,596,408 and U.S. Pat. No. 6,771,373), in which the turbidity level of water is determined by detecting the light beam transmitted through the cleaning medium. Curve A shows a plot of the signal values obtained by a conventional turbidity sensor under a low turbidity situation (i.e. the turbidity of 0~200 NTU), and Curve B shows a plot of the signal values taken from the water quality sensor of the present invention under the same range of turbidity. As shown in FIG. 12, Curve A shows that the signal value of turbidity measurement is substantially unchanged, meaning the conventional turbidity sensor failing to work under the range of 0~200 NTU. Compared to Curve A, Curve B clearly shows the difference in signal values under such low turbidity situation, meaning that the sensor module of the present invention works well even under such low turbidity situation. Therefore, the accuracy of detection for the water quality sensor of the present invention is improved.

The water quality sensor of the present invention includes an optical sensor which utilizes the backscattered light generated from a detecting beam emitting from the light emitting element and backscattered by the cleaning medium to determine the turbidity level of the cleaning medium in the household appliances, thereby enhancing the accuracy of turbidity detection. The water sensor according to the present invention is capable of reducing the fouling on the sensor with a simple structure, such that the life-time of the sensor is improved.

The embodiments were chosen and described in order to best explain the principles of the disclosure and its practical applications, to thereby enable others skilled in the art to best utilize the disclosure and various embodiments with various modifications as are suited to the particular use contemplated. The embodiments depicted above and the appended drawings are exemplary and are not intended to be exhaustive or to limit the scope of the present disclosure to the precise forms disclosed. Many modifications and variations are possible in view of the above teachings.

Therefore, except for particularly distinct features, any feature disclosed herein is an example of identical or similar features. With the preferred embodiments described above, a person skilled in the art understands that the present invention possesses novelty, inventive step and practical applicability. Any modification to the present invention (e.g. a modification to the securing method or securing location) without departing from the scope of the claims can be made by a person skilled in the art.

What is claimed is:

1. A water quality sensor for a household appliance, comprising:
   a housing forming an inner space and having at least one transparent panel in contacting to a cleaning medium of said household appliance;
   a circuit board having a microcontroller configured thereon, said circuit board being positioned within said inner space and housed by said housing;
   a light emitting element configured on said circuit board for emitting a detecting beam passing through said transparent panel;
   a light receiving element configured on said circuit board for receiving a backscattered beam generated from said detecting beam and backscattered by said cleaning medium; and
   a sensor holder attached to said circuit board and receiving said light emitting element and said light receiving element therein, said sensor holder having a plurality of non-transparent walls surrounding said light emitting element and said light receiving element, and a first opening for the detecting beam to pass and a second opening for the light receiving element to receive the light in a straight ahead direction, said first and second openings being formed on a top of said sensor holder,
   wherein said light emitting element and said light receiving element configured on said circuit board are positioned on and facing a same plane, and said detecting beam emitted from said light emitting element is blocked by said sensor holder from being directly received by said light receiving element and only passes said opening of said sensor holder, such that said water quality sensor determines the water quality of said cleaning medium contained in said household appliance based on said backscattered beam received by said light receiving element.

2. The water quality sensor of claim 1, further comprising an electrical sensor for determining a conductivity of said cleaning medium.

3. The water quality sensor of claim 2, wherein said electrical sensor comprises at least one electrode to discharge in said cleaning medium.

4. The water quality sensor of claim 3, wherein said transparent panel is formed with a window portion, and wherein said at least one electrode is extended through said window portion and electrically contacted with said cleaning medium.

5. The water quality sensor of claim 3, wherein said housing is formed with at least one concave portion and a corresponding through-hole, and wherein said at least one electrode is contained within said at least one concave portion and extended through said through-hole.

6. The water quality sensor of claim 2, further comprising an analog-to-digital converter to convert an analog signal transmitted from said electrical sensor to a digital signal.

7. The water quality sensor of claim 6, wherein said analog-to-digital converter is separated from said microcontroller and electrically connected thereto.

8. The water quality sensor of claim 6, wherein said analog-to-digital converter is built in said microcontroller.

9. The water quality sensor of claim 1, wherein said circuit board is positioned on a plane parallel to said transparent panel, such that said detecting beam passes along a path perpendicular to a flow direction of said cleaning medium.

10. The water quality sensor of claim 1, wherein said top of said sensor holder is apart from said transparent panel by less than 5 mm.

11. The water quality sensor of claim 1, wherein each of said non-transparent walls has a thickness ranged from 1 mm to 5 mm, and a height ranged from 2 mm to 10 mm.

12. The water quality sensor of claim 1, wherein a distance between of said light emitting element and said light receiving element is ranged from 3 mm to 10 mm.

13. The water quality sensor of claim 1, wherein said housing comprises a base and a cover attached thereto, and wherein said transparent panel is configured on said base at a side opposite to said cover.

14. The water quality sensor of claim 1, wherein said water quality is a turbidity level of said cleaning medium.

15. The water quality sensor of claim 1, wherein said household appliance is one of a dishwasher and a laundry machine.

\* \* \* \* \*